United States Patent [19]

Venturello et al.

[11] 3,980,675

[45] Sept. 14, 1976

[54] PROCESS FOR PREPARING 2,5-DIMETHYL-3-(2H)-FURANONE

[75] Inventors: Carlo Venturello, Turin; Rino D'Aloisio, Novara, both of Italy

[73] Assignee: Montedison S.p.A., Milan, Italy

[22] Filed: Feb. 14, 1975

[21] Appl. No.: 550,137

[30] Foreign Application Priority Data

Feb. 15, 1974 Italy .................................. 41004/74

[52] U.S. Cl. .......................... 260/347.8; 260/310 A; 260/159; 8/162 B; 8/180
[51] Int. Cl.² ..................................... C07D 307/58
[58] Field of Search ................................ 260/347.8

[56] References Cited

OTHER PUBLICATIONS

Yankeelov, Biochemistry, vol. 9, pp. 2433–2439 (1970).

*Primary Examiner*—Harry I. Moatz

[57] ABSTRACT

There is disclosed a simple, economical process for preparing 2,5-dimethyl-3-(2H)-furanone by hydrolysis of the dimer of diacetyl at a temperature of 20°C to 120°C and in the presence of an acid, mineral or organic, or of a cationic resin, with elimination of a acetic acid.

3 Claims, No Drawings

PROCESS FOR PREPARING 2,5-DIMETHYL-3-(2H)-FURANONE

THE PRIOR ART

It is known that 2,5-dimethyl-3-(2h)-furanone which is useful as an intermediate for the preparation of azoic dyes, in organic syntheses in general, and in perfumes, can be prepared by the following sequence of steps:
1. conversion of ethyl-2,5-dimethyl-furan-3-carboxylate to the corresponding hydrazide;
2. conversion of the hydrazide to the corresponding furoylazide;
3. conversion of the azide to the corresponding benzyl-o-isopropylurethane; and
4. hydrolysis of said urethane.

Because it is multi-stage and requires the four operations, that process is economically and industrially burdensome.

THE PRESENT INVENTION

An object of this invention is to provide a simple, economical process for preparing 2,5-dimethyl-3-(2H)-furanone.

This and other objects are achieved by the present invention in accordance with which the dimer of diacetyl is hydrolyzed at a temperature of 20°C to 120°C and in the presence of an acid, mineral or organic, or of a cation-exchange resin.

The starting diacetyl dimer in the aldolic form has the general formula $C_8H_{12}O_4$ and the structural formula:

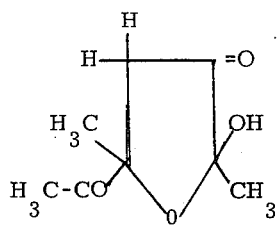

(5-acetyl-tetrahydro-2-hydroxy-2,5-dimethyl-3-oxofurane). It is obtained by aldolic condensation of the diacetyl by known methods.

We have found that while hydrolysis of the diacetyl dimer to 2,5-dimethyl-3-(2H)-furanone having the formula

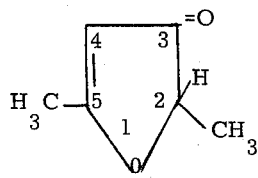

may occur, even if slowly, if the diacetyl dimer is exposed to water for a long period of time, the hydrolysis is considerably accelerated at temperatures in the range 20°C to 120°C and in the presence of mineral or organic acids or of cationic resins.

Moreover, we have found that the hydrolysis of the diacetyl dimer to 2,5-dimethyl-3-(2H)-furanone can be effected in the same solution in which the aldolic condensation of the diacetyl is carried out, without preliminary separation of the condensation product (diacetyl dimer).

The speed of the hydrolysis, and the yield of 2,5-dimethyl-3-(2H)-furanone, are functions of several factors which are independent of each other so far as concerns the temperature, concentration of the acid used to catalyze the hydrolysis, type of acid used and duration of the reaction.

On the contrary, variations in the concentration of the starting diacetyl dimer do not appear to significantly affect the yield of 2,5-dimethyl-3-(2H)-furanone, at least within the range of parameters for converting the diacetyl dimer to the furanone in accordance with the preferred embodiments of the present invention and which are as follows:
  a. temperature: comprised between 20°C and 120°C;
  b. concentration of dimer: (in gms/100 cc of solution) comprised between 3 and 11 calculated on 100 percent conversion of the diacetyl in the aldolic condensation;
  c. acid concentration: (in gms/100 cc of solution) comprised between 0.04 and 4.0;
  d. duration of reaction: comprised between 1 and 8 hours.

Acids which are particularly suitable for use in the present process, because of both effectiveness and ready availability, are:
hydrochloric acid, preferably concentrated;
sulphuric acid at 50 percent concentration;
formic acid;
glacial acetic acid; and
cation-exchange resins (in equivalent amounts).

The hydrolysis product can be readily extracted from the aqueous solution in which it is formed and which, optionally, may be saturated with a mineral salt such as, for instance NaCl or the like, by means of solvents such as ethyl ether, chloroform, 1,2-dichloroethane, etc. by conventional extracting techniques.

From the extract, after separation by distillation under vacuum of a first fraction consisting of 2,5-dimethyl-3-(2H)-furanone, there may be obtained further distillation, a second fraction containing, in part, unconverted diacetyl dimer and, in part, dimer which may have been formed by degradation of the heavier condensation products under heating during the distillation.

In a presently preferred embodiment of the invention, the diacetyl dimer is converted to the 2,5-dimethyl-3-(2H)-furanone in the aqueous solution in which the diacetyl is converted to the dimer by aldolic condensation by heating said solution containing the dimer, in a concentration of 3 to 11 calculated as stated hereinabove, at about 95°C for about 6 hours in the presence of concentrated HCl in an amount of 0.30 – 0.38 g/100 cc of the aqueous solution.

In said presently preferred embodiment, the yield of 2,5-dimethyl-3-(2H)-furanone obtained is from 60 to 70 percent in respect to the starting diacetyl dimer. That corresponds to a high conversion of the diacetyl dimer present in the aqueous solution to 2,5-dimethyl-3-(2H)-furanone. As has been reported in the art, the yield of dimer resulting from aldolic condensation of diacetyl by known methods is 50 to 60 percent with respect to the diacetyl and calculated on the amount of the dimer obtained by distillation.

On the other hand, hydrolyses of pure dimer under the conditions of this invention have confirmed a conversion yield of the diacetyl dimer to 2,5-dimethyl-3-(2H)-furanone of about 90 percent.

The process of this invention is particularly advantageous, due to the mild operating conditions which it involves.

A further advantage resides in the simplicity of the chemical conversion (hydrolysis) of the diacetyl dimer to 2,5-dimethyl-3-(2H)-furanone in the same aqueous solution in which the dimer is formed by aldolic condensation of the diacetyl, in contrast to the four-stage process of the prior art referred to hereinabove.

The following examples are given to further illustrate the invention and are not intended to be limiting.

Example 2 illustrates the process of the invention applied to the diacetyl dimer prepared separately and for the purpose of demonstrating the high conversion rates obtained by this process. Example 4 illustrates the use of the acid hydrolysis product in the preparation of pigments.

EXAMPLE 1

49 g of diacetyl (50 cc) were dissolved in 250 cc of $H_2O$ in a 600 cc beaker. 9.8 g of KOH, dissolved in 175 cc of $H_2O$, were dripped into the diacetyl solution, kept under stirring and maintained at a temperature between 2° and 5°C.

At the end of the dripping and after stopping the cooling, the solution was neutralized with $H_2SO_4$ at 50 percent. To the solution (442 cc) there were admixed 4 cc of concentrated HCl (density 1.18) and the solution was then heated under slow stirring for 6 hours at 95°C. At the end of this operation, the pH of the solution was brought to 5 – 6 with 30 % NaOH, saturated with NaCl (140 g), and extracted 5 times with ether.

The etheric solution was thereupon dried on $Na_2SO_4$. By distillation of the ether, 34.6 g of residue were obtained which, by distillation under vacuum (at 69° – 70°C/12 mm Hg), yielded 19.47 g of 2,5-dimethyl-3-(2H)-furanone. The yield, with respect to the starting diacetyl, amounted to 61 percent.

The gas-chromatographic determination of the etheric extract (internal standard: naphthalene) gave a yield in 2,5-dimethyl-3-(2H)-furanone of 70 percent.

The elementary analysis, calculated for $C_6H_8O_2$, gave the following values: C = 64.00%; H = 7.18%. The theoretical values were: C = 64.21%; H = 7.46%.

The I.R. spectrum showed intense absorptions at 1712 and 1616 cm$^{-1}$. The U.V. spectrum showed a $\lambda_{max}$ at 260 m$\mu$. The I.R., U.V. and N.M.R. spectra were in accordance with the values reported in the literature for 2,5-dimethyl-3-(2H)-furanone.

EXAMPLE 2

To a solution of 14 g of diacetyl dimer dissolved in 220 cc $H_2O$ there added 2 cc of concentrated HCl, and the mixture was heated under slow stirring for 6 hours at 95°C. At the end of this operation, the product was worked up as in Example 1.

Thereby were obtained 8.40 g of a raw product containing 97 percent of 2,5-dimethyl-3-(2H)-furanone (by gas-chromatographic analysis). The yield with respect to the startng dimer amounted to 89.3 percent.

EXAMPLE 3

12.25 g (12.5 cc) of diacetyl were converted to dimer as in Example 1. To the solution (120 cc) there were added 10 cc of a suspension of cationic resin Dowex 50 W × 8, 100/200 mesh, and the mass was heated for 6 hours at 95°C under stirring.

At the end of this operation, the solution was neutralized with 30 percent NaOH, the resin was filtered and the aqueous solution was saturated with 35 g of NaCl, whereupon it was extracted three times with ether. By distillation of the ether, 10.1 g of residue were obtained, which by distillation yielded 4.5 g of product. The yield with respect to the starting diacetyl amounted to 56.4 percent.

EXAMPLE 4

Preparation of 1N, 1N'-p-phenylene-bis-(5-methyl-3-pyrazolone).

Into a 100 cc flask, fitted with a mechanical stirrer, a cooler and a dripper, there were introduced 7 g of tetrazonium sulphate of p-phenylendiamine and 30 cc of dimethoxyethane. Into this mixture, cooled with ice and maintained under stirring, there were slowly dripped 11 g of 2,5-dimethyl-3-(2H)-furanone. At the end of the drippping the cooling was further maintained with ice for ½ hour.

The ice bath was then removed and the mixture, still under stirring, was left to rest at room temperature for one hour and a half. Subsequently, the temperature was gradually raised to 50° – 60°C and then maintained at that level for 2 hours.

At the end of the test the solid thus obtained was gathered onto a filter and repeatedly washed with acetone until the acetone remained colorless. The solid was then dissolved in a 10 percent NaOH aqueous solution. The alkaline solution was repeatedly extracted, first with ether and then with chloroform. Thereupon, by addition of 10 percent aqueous solution of HCl to the alkaline solution until neutralization was attained, the bis-pyrazolone precipitated, 4.5 g of raw product being obtained. This product was purified by dissolution in acetic anhydride-acetic acid, by a subsequent separation of the solid O-acetyl thus formed from the bis-pyrazolone, and by further purification of the latter.

By saponification of the O-acetyl with 10 percent aqueous NaOH and by subsequent neutralization of the alkaline solution with HCl at 10 percent, the purified bis-pyrazolone (3 g) precipitated.

Coupling of the 1N, 1N'-p-phenylen-bis-(5-methyl-3-pyrazolone).

1.35 g (1/200 moles) of the purified bis-pyrazolone were dissolved in an aqueous solution of 10% KOH (7 – 8 cc) under heating. After cooling, the solution was diluted to 70 – 80 cc and to it there were added 1 g of $K_2CO_3$ and 10 cc of pyridine. The pH of the solution was comprised between 11 and 13.

1.62 g (1/100 mole) of 2,4-dichloroaniline were dissolved, under stirring and heating, in 5 cc of concentrated HCl and 20 cc of $H_2O$. This solution was rapidly cooled down under stirring. To it there were added 10 g of ice and then, under stirring, 10 cc of a normal solution of $NaNO_2$ were slowly dripped in over a period of 10 – 15 minutes. (If necessary, the solution thus obtained was filtered).

Any excess $NaNO_2$ was eliminated with sulphamic acid. The acid diazonium solution was dripped, in 5 – 10 minutes, into the alkaline solution of the bis-pyrazolone, maintained at room temperature and under stirring. The pH of the alkaline solution, which dropped during the dripping of the diazonium, had to be brought back continuously to the initial values of 11 – 13 by gradual addition of an aqueous solution of KOH.

At the end of the coupling the solution was neutralized with 10 percent aqueous HCl. The solid was filtered and then washed with copious amounts of water. Thereupon the solid was suspended in acetone for a first cleaning. It was filtered and the solid obtained was repeatedly refluxed with acetone until the acetone remained colorless. The product was kept in suspension, under stirring, in cyclohexanone at a suitable temperature until it acquired the desired pigmentary form. Thereby were obtained 2.1 g of product (a yellow-orange powder). The elementary analysis, calculated for the $C_{26}H_{18}N_8O_2Cl_4$, gave the following results:

| | | |
|---|---|---|
| C | = | 50.45% |
| H | = | 2.77% |
| N | = | 17.90% |
| Cl | = | 22.75%. |

The theoretical values are:

| | | |
|---|---|---|
| C | = | 50.65% |
| H | = | 2.92% |
| N | = | 18.18% |
| Cl | = | 23.05%. |

Dyeing Example

A mixture was prepared consisting of:
100 g of polyvinyl chloride obtained by suspension polymerization;
1.5 g of a complex salt of Ba or Cd of a higher fatty acid with a complexing and anti-oxidizing action;
3 g of epoxidated soya oil; and
2 g of $TiO_2$.
0.1 g of pigment obtained by coupling the bis-pyrazolone with the diazonium salt of 2,4-dichloroaniline was treated with said mixture for 10 minutes at 180°C in a three-cylinder refiner, according to techniques and formulations known per se.

The manufactured article thus obtained had a yellow-orange coloring of good intensity, good heat stability, and resistance to common solvents.

Following a similar procedure and by using diazonium salts of p-chloroaniline, of the 2,4,5-trichloroaniline type, other bis-pyrazolone coupling products were prepared.

These products have pigmenting properties. To obtain the best pigments, it is convenient to condition the pigments thus prepared with suitable solvents, such as cyclohexanone.

These pigments have a yellow or yellow-orange shade of good intensity as well as good general characteristics, especially good heat-stability and resistance to solvents.

They are useful, according to known techniques:
1. for bulk-dyeing artificial and synthetic textile fibers;
2. for dyeing plastic materials, e.g., polyethylenic and polychloroethylenic materials;
3. in the preparation of varnishes; and
4. in the preparation of inks.

We claim:
1. The process for preparing 2,5-dimethyl-3-(2H)-furanone which comprises subjecting diacetyl dimer, 5-acetyl-tetrahydro-2-hydroxy-2,5-dimethyl-3-oxofurane, to hydrolysis in an aqueous solution containing the dimer in a concentration of from 3 to 11 grams thereof per 100 cc of the solution and from 0.04 to 4.0 grams of an acidic catalyst per 100 cc of solution, at a temperature of from 20°C to 120°C, and for a reaction time of from 1 to 8 hours.
2. The process of claim 1, in which the aqueous solution in which the diacetyl dimer is subjected to the acid hydrolysis is the solution resulting from conversion of diacetyl to the dimer by aldolic condensation of the diacetyl.
3. The process of claim 2, in which the acidic catalyst is hydrochloric acid, sulphuric acid, formic acid, glacial acetic acid or an equivalent amount of a cation-exchange resin.

* * * * *

UNITED STATES PATENT OFFICE
CERTIFICATE OF CORRECTION

Patent No. 3,980,675      Dated September 14, 1976

Inventor(s) Carlo VENTURELLO et al

It is certified that error appears in the above-identified patent and that said Letters Patent are hereby corrected as shown below:

Col. 1, line 1,    "2,5-dimethyl-3-(2h)-furanone" should be

- - - 2,5-dimethyl-3-(2H)-furanone - - -.

Signed and Sealed this

*twelfth* Day of *July 1977*

[SEAL]

*Attest:*

RUTH C. MASON
*Attesting Officer*

C. MARSHALL DANN
*Commissioner of Patents and Trademarks*